(12) United States Patent
Poppe et al.

(10) Patent No.: US 10,869,762 B2
(45) Date of Patent: Dec. 22, 2020

(54) MEDICAL DEVICE WITH INNER ASSEMBLY

(71) Applicant: BOSTON SCIENTIFIC SCIMED, INC., Maple Grove, MN (US)

(72) Inventors: Kevin Robert Poppe, New Brighton, MN (US); Daniel J. Foster, Lino Lakes, MN (US); Bradley S. Swehla, Eagan, MN (US); Christopher Jay Scheff, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 275 days.

(21) Appl. No.: 15/921,033

(22) Filed: Mar. 14, 2018

(65) Prior Publication Data

US 2018/0263773 A1 Sep. 20, 2018

Related U.S. Application Data (60) Provisional application No. 62/471,075, filed on Mar. 14, 2017.

(51) Int. Cl.
*A61F 2/24* (2006.01)
*A61F 2/966* (2013.01)
(Continued)

(52) U.S. Cl.
CPC .......... *A61F 2/2439* (2013.01); *A61F 2/2436* (2013.01); *A61F 2/966* (2013.01);
(Continued)

(58) Field of Classification Search
CPC ...... A61F 2/966; A61F 2/2439; A61F 2/2436; A61F 2230/0091; A61F 2002/9534;
(Continued)

(56) References Cited

U.S. PATENT DOCUMENTS 3,674,014 A 7/1972 Tillander
4,798,598 A 1/1989 Bonello et al.
(Continued)

FOREIGN PATENT DOCUMENTS

EP 0778040 A2 6/1997
JP 2012501725 B2 1/2012
(Continued)

OTHER PUBLICATIONS

International Search Report and Written Opinion dated Mar. 2, 2018 for International Application No. PCT/US2017/062113.
(Continued)

*Primary Examiner* — Phong Son H Dang
(74) *Attorney, Agent, or Firm* — Seager, Tufte & Wickhem LLP (57) ABSTRACT

Medical devices and methods for making and using medical devices are disclosed. An example system for delivering an implantable medical device includes an outer shaft having a proximal end, a distal portion and a lumen extending therein. The system includes an inner catheter, wherein the inner catheter extends within at least a portion of the lumen of the outer shaft. The system also includes an actuation shaft extending within a portion of the lumen of the inner shaft, wherein a distal end of the actuation shaft is coupled to a coupling member. The system also includes a plurality of translation members coupled to the implantable medical device and the coupling member. The system also includes a grouping coil wound around at least a portion of each of the plurality of translation members.

19 Claims, 6 Drawing Sheets

(51) Int. Cl.
 *A61M 25/09* (2006.01)
 *A61M 25/00* (2006.01)
 *A61F 2/95* (2013.01)

(52) U.S. Cl.
 CPC ..... *A61F 2/9517* (2020.05); *A61F 2002/9511* (2013.01); *A61F 2002/9534* (2013.01); *A61F 2002/9665* (2013.01); *A61F 2230/0091* (2013.01); *A61M 25/0021* (2013.01); *A61M 25/09* (2013.01); *A61M 2025/0004* (2013.01)

(58) Field of Classification Search
 CPC ............ A61F 2002/9665; A61F 2/9517; A61F 2002/9511; A61M 25/0021; A61M 2025/0004; A61M 25/09
 See application file for complete search history.

(56) References Cited

U.S. PATENT DOCUMENTS

| | | | |
|---|---|---|---|
| 4,955,384 A | 9/1990 | Taylor et al. | |
| 4,985,022 A | 1/1991 | Fearnot et al. | |
| 4,998,923 A | 3/1991 | Samson et al. | |
| 5,003,989 A | 4/1991 | Taylor et al. | |
| 5,035,706 A * | 7/1991 | Giantureo | A61F 2/86 606/198 |
| 5,095,915 A | 3/1992 | Engelson | |
| 5,315,996 A | 5/1994 | Lundquist | |
| 5,406,960 A | 4/1995 | Corso, Jr. | |
| 5,437,288 A | 8/1995 | Schwartz et al. | |
| 5,570,701 A | 11/1996 | Ellis et al. | |
| 5,599,492 A | 2/1997 | Engelson | |
| 5,665,115 A * | 9/1997 | Cragg | A61F 2/90 623/1.13 |
| 5,746,701 A | 5/1998 | Noone | |
| 5,749,837 A | 5/1998 | Palermo et al. | |
| 5,769,796 A | 6/1998 | Palermo et al. | |
| 5,772,609 A | 6/1998 | Nguyen et al. | |
| 5,776,080 A | 7/1998 | Thome et al. | |
| 5,800,456 A * | 9/1998 | Maeda | A61F 2/88 623/1.15 |
| 5,833,632 A | 11/1998 | Jacobsen et al. | |
| 5,902,254 A | 5/1999 | Magram | |
| 5,931,830 A | 8/1999 | Jacobsen et al. | |
| 5,951,494 A | 9/1999 | Wang et al. | |
| 6,001,068 A | 12/1999 | Uchino et al. | |
| 6,017,319 A | 1/2000 | Jacobsen et al. | |
| 6,139,510 A | 10/2000 | Palermo | |
| 6,221,096 B1 * | 4/2001 | Aiba | A61F 2/86 606/108 |
| 6,254,628 B1 * | 7/2001 | Wallace | A61B 17/12118 623/1.12 |
| 6,273,876 B1 | 8/2001 | Klima et al. | |
| 6,565,597 B1 * | 5/2003 | Fearnot | A61F 2/07 623/1.13 |
| 6,606,921 B2 | 8/2003 | Noetzold | |
| 6,739,787 B1 | 5/2004 | Bystrom | |
| 6,764,503 B1 * | 7/2004 | Ishimaru | A61F 2/07 606/108 |
| 6,918,882 B2 | 7/2005 | Skujins et al. | |
| 6,921,397 B2 | 7/2005 | Corcoran et al. | |
| 7,055,656 B2 | 6/2006 | Drew | |
| 7,074,197 B2 | 7/2006 | Reynolds et al. | |
| 7,338,495 B2 | 3/2008 | Adams | |
| 7,413,563 B2 | 8/2008 | Corcoran et al. | |
| 7,533,906 B2 | 5/2009 | Luettgen et al. | |
| 7,540,865 B2 | 6/2009 | Griffin et al. | |
| 7,579,550 B2 | 8/2009 | Dayton et al. | |
| 7,618,379 B2 | 11/2009 | Reynolds et al. | |
| 7,625,364 B2 | 12/2009 | Corcoran et al. | |
| 7,780,611 B2 | 8/2010 | Griego et al. | |
| 7,784,376 B2 | 8/2010 | Wen | |
| 7,824,345 B2 | 11/2010 | Euteneuer et al. | |
| 7,841,994 B2 | 11/2010 | Skujins et al. | |
| 7,850,623 B2 | 12/2010 | Griffin et al. | |
| 7,854,109 B2 | 12/2010 | Zubiate et al. | |
| 7,914,466 B2 | 3/2011 | Davis et al. | |
| 7,914,467 B2 | 3/2011 | Layman et al. | |
| 7,918,080 B2 | 4/2011 | Zubiate et al. | |
| 7,993,286 B2 | 8/2011 | Reynolds et al. | |
| 8,022,331 B2 | 9/2011 | Reynolds et al. | |
| 8,047,236 B2 | 11/2011 | Perry | |
| 8,048,004 B2 | 11/2011 | Davis et al. | |
| 8,048,060 B2 | 11/2011 | Griffin et al. | |
| 8,080,053 B2 * | 12/2011 | Satasiya | A61F 2/91 623/1.15 |
| 8,099,939 B2 | 1/2012 | Zubiate et al. | |
| 8,100,031 B2 | 1/2012 | Zubiate et al. | |
| 8,105,246 B2 | 1/2012 | Voeller et al. | |
| 8,124,876 B2 | 2/2012 | Dayton et al. | |
| 8,137,293 B2 | 3/2012 | Zhou et al. | |
| 8,147,534 B2 * | 4/2012 | Berez | A61B 17/12022 623/1.11 |
| 8,157,751 B2 | 4/2012 | Adams et al. | |
| 8,182,465 B2 | 5/2012 | Griffin et al. | |
| 8,192,422 B2 | 6/2012 | Zubiate et al. | |
| 8,197,419 B2 | 6/2012 | Field et al. | |
| 8,231,551 B2 | 7/2012 | Griffin et al. | |
| 8,257,279 B2 | 9/2012 | Davis et al. | |
| 8,292,829 B2 | 10/2012 | Griego et al. | |
| 8,317,777 B2 | 11/2012 | Zubiate et al. | |
| 8,328,868 B2 * | 12/2012 | Paul | A61F 2/24 623/2.11 |
| 8,376,865 B2 | 2/2013 | Forster et al. | |
| 8,376,961 B2 | 2/2013 | Layman et al. | |
| 8,377,035 B2 | 2/2013 | Zhou et al. | |
| 8,397,481 B2 | 3/2013 | Zubiate et al. | |
| 8,409,114 B2 | 4/2013 | Parins | |
| 8,414,506 B2 | 4/2013 | Reynolds et al. | |
| 8,425,408 B2 | 4/2013 | Boulais et al. | |
| 8,443,692 B2 | 5/2013 | Zubiate et al. | |
| 8,449,526 B2 | 5/2013 | Snyder et al. | |
| 8,459,138 B2 | 6/2013 | Zubiate et al. | |
| 8,475,366 B2 | 7/2013 | Boulais et al. | |
| 8,485,992 B2 | 7/2013 | Griffin et al. | |
| 8,535,219 B2 | 9/2013 | Smith et al. | |
| 8,535,243 B2 | 9/2013 | Shireman | |
| 8,551,020 B2 | 10/2013 | Chen et al. | |
| 8,551,021 B2 | 10/2013 | Voeller et al. | |
| 8,556,914 B2 | 10/2013 | Vrba | |
| 8,608,648 B2 | 12/2013 | Banik et al. | |
| 8,622,894 B2 | 1/2014 | Banik et al. | |
| 8,636,716 B2 | 1/2014 | Griffin et al. | |
| 8,656,697 B2 | 2/2014 | Zubiate et al. | |
| 8,677,602 B2 | 3/2014 | Dayton et al. | |
| 8,758,268 B2 | 6/2014 | Bown et al. | |
| 8,784,337 B2 | 7/2014 | Voeller et al. | |
| 8,795,202 B2 | 8/2014 | Northrop et al. | |
| 8,795,254 B2 | 8/2014 | Layman et al. | |
| 8,821,477 B2 | 9/2014 | Northrop et al. | |
| 8,833,197 B2 | 9/2014 | Zubiate et al. | |
| 8,845,552 B2 | 9/2014 | Greigo et al. | |
| 8,864,654 B2 | 10/2014 | Kleiner et al. | |
| 8,870,790 B2 | 10/2014 | Davis et al. | |
| 8,900,163 B2 | 12/2014 | Jacobsen et al. | |
| 8,915,865 B2 | 12/2014 | Jacobsen et al. | |
| 8,932,235 B2 | 1/2015 | Jacobsen et al. | |
| 8,936,558 B2 | 1/2015 | Jacobsen et al. | |
| 8,939,916 B2 | 1/2015 | Jacobsen et al. | |
| 8,945,096 B2 | 2/2015 | Zubiate et al. | |
| 9,005,114 B2 | 4/2015 | Zubiate et al. | |
| 9,011,318 B2 | 4/2015 | Choset et al. | |
| 9,023,011 B2 | 5/2015 | Griffin et al. | |
| 9,072,874 B2 | 7/2015 | Northrop et al. | |
| 9,370,432 B2 | 6/2016 | Zubiate et al. | |
| 9,375,234 B2 | 6/2016 | Vrba | |
| 9,386,911 B2 | 7/2016 | Zubiate et al. | |
| 9,387,308 B2 | 7/2016 | Hinchliffe et al. | |
| 9,387,309 B2 | 7/2016 | Parodi et al. | |
| 9,402,682 B2 | 8/2016 | Worrell et al. | |
| 9,993,360 B2 * | 6/2018 | Shalev | A61F 2/962 |
| 10,092,426 B2 * | 10/2018 | McHugo | A61F 2/90 |
| 10,258,465 B2 * | 4/2019 | Salahieh | A61F 2/2439 |
| 10,646,365 B2 * | 5/2020 | Berra | A61F 2/07 |

(56) References Cited

U.S. PATENT DOCUMENTS

| | | |
|---|---|---|
| 2003/0069520 A1 | 4/2003 | Skujins et al. |
| 2003/0069521 A1 | 4/2003 | Reynolds et al. |
| 2004/0220499 A1 | 11/2004 | Griego et al. |
| 2004/0243143 A1 | 12/2004 | Corcoran et al. |
| 2005/0080400 A1 | 4/2005 | Corcoran et al. |
| 2005/0090848 A1 | 4/2005 | Adams |
| 2005/0267444 A1 | 12/2005 | Griffin et al. |
| 2006/0111615 A1 | 5/2006 | Danitz et al. |
| 2006/0122537 A1 | 6/2006 | Reynolds et al. |
| 2006/0179966 A1 | 8/2006 | Kuo |
| 2006/0189896 A1 | 8/2006 | Davis et al. |
| 2007/0049902 A1 | 3/2007 | Griffin et al. |
| 2007/0066900 A1 | 3/2007 | O'Keeffe |
| 2007/0083132 A1 | 4/2007 | Sharrow |
| 2007/0100285 A1 | 5/2007 | Griffin et al. |
| 2007/0114211 A1 | 5/2007 | Reynolds et al. |
| 2007/0135734 A1 | 6/2007 | Reynolds et al. |
| 2007/0233043 A1 | 10/2007 | Dayton et al. |
| 2007/0244414 A1 | 10/2007 | Reynolds et al. |
| 2008/0064989 A1 | 3/2008 | Chen et al. |
| 2008/0077119 A1 | 3/2008 | Snyder et al. |
| 2008/0194994 A1 | 8/2008 | Bown et al. |
| 2008/0205980 A1 | 8/2008 | Zubiate et al. |
| 2008/0245173 A1 | 10/2008 | Schwerin et al. |
| 2008/0262474 A1 | 10/2008 | Northrop |
| 2009/0036833 A1 | 2/2009 | Parins |
| 2009/0043228 A1 | 2/2009 | Northrop et al. |
| 2009/0043283 A1 | 2/2009 | Turnlund et al. |
| 2009/0143768 A1 | 6/2009 | Parodi et al. |
| 2009/0156999 A1 | 6/2009 | Adams et al. |
| 2009/0171151 A1 | 7/2009 | Choset et al. |
| 2009/0312606 A1 | 12/2009 | Dayton et al. |
| 2009/0319037 A1* | 12/2009 | Rowe ............... A61F 2/2436 623/2.11 |
| 2010/0063480 A1 | 3/2010 | Shireman |
| 2010/0076266 A1 | 3/2010 | Boulais et al. |
| 2010/0080892 A1 | 4/2010 | O'Brien et al. |
| 2010/0145308 A1 | 6/2010 | Layman et al. |
| 2010/0249655 A1 | 9/2010 | Lemon |
| 2010/0274187 A1* | 10/2010 | Argentine ......... A61M 25/0082 604/96.01 |
| 2010/0286566 A1 | 11/2010 | Griffin et al. |
| 2010/0294071 A1 | 11/2010 | Zubiate et al. |
| 2010/0305475 A1 | 12/2010 | Hinchliffe et al. |
| 2011/0056320 A1 | 3/2011 | Zubiate et al. |
| 2011/0082443 A1 | 4/2011 | Griffin et al. |
| 2011/0152613 A1 | 6/2011 | Zubiate et al. |
| 2011/0178588 A1 | 7/2011 | Haselby |
| 2011/0184241 A1 | 7/2011 | Zubiate et al. |
| 2011/0218620 A1* | 9/2011 | Meiri ............... A61B 17/12013 623/2.11 |
| 2011/0257478 A1 | 10/2011 | Kleiner et al. |
| 2011/0264191 A1 | 10/2011 | Rothstein |
| 2012/0160537 A1 | 6/2012 | Wen |
| 2013/0085562 A1* | 4/2013 | Rincon ............... A61F 2/95 623/1.11 |
| 2013/0123912 A1 | 5/2013 | Tung et al. |
| 2013/0131775 A1* | 5/2013 | Hadley ............... A61F 2/966 623/1.11 |
| 2014/0235361 A1 | 8/2014 | Forster et al. |
| 2016/0184117 A1* | 6/2016 | Vad ............... A61F 2/966 623/1.11 |
| 2018/0140323 A1 | 5/2018 | Foster et al. |

FOREIGN PATENT DOCUMENTS

| | | |
|---|---|---|
| JP | 5575840 B2 | 8/2014 |
| WO | 2006041612 A2 | 4/2006 |
| WO | 2006073581 A2 | 7/2006 |
| WO | 2016196933 A1 | 12/2016 |

OTHER PUBLICATIONS

International Search Report and Written Opinion dated Jun. 15, 2018 for International Application No. PCT/US2018/022377.

* cited by examiner

MEDICAL DEVICE WITH INNER ASSEMBLY

CROSS-REFERENCE TO RELATED APPLICATIONS

This application claims the benefit of priority under 35 U.S.C. § 119 to U.S. Provisional Application Ser. No. 62/471,075, filed Mar. 14, 2017, the entirety of which is incorporated herein by reference.

TECHNICAL FIELD

The present disclosure pertains to medical devices, and methods for manufacturing medical devices. More particularly, the present disclosure pertains to medical devices including an inner assembly designed to reduce the profile of the medical device.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example system for delivering an implantable medical device comprises an outer shaft having a proximal end, a distal portion and a lumen extending therein. The system includes an inner catheter having a proximal end, a distal portion and a lumen extending therein, wherein the inner catheter extends within at least a portion of the lumen of the outer shaft. The system also includes an actuation shaft extending within a portion of the lumen of the inner shaft, wherein a distal end of the actuation shaft is coupled to a proximal portion of a coupling member. The system also includes a plurality of translation members each having a proximal end and a distal end, wherein the distal ends of the translation members are coupled to the implantable medical device, and wherein the proximal ends of the translation members are coupled to a distal portion of the coupling member. The system also includes a grouping coil wound around at least a portion of each of the plurality of translation members.

Alternatively or additionally to any of the embodiments above, wherein the actuation shaft, the plurality of translation members and the coupling member are configured to translate along the longitudinal axis of the inner catheter.

Alternatively or additionally to any of the embodiments above, wherein a length of the grouping coil is configured to adjust as the coupling member translates along the longitudinal axis of the inner catheter.

Alternatively or additionally to any of the embodiments above, wherein the grouping coil is designed to group the plurality of translation members as the translation members translate along the longitudinal axis of the inner catheter.

Alternatively or additionally to any of the embodiments above, further comprising a containment fitting attached to the distal portion of the inner catheter, wherein the containment fitting is configured to limit a distal end of the grouping coil from translating distally.

Alternatively or additionally to any of the embodiments above, wherein the grouping coil is positioned between the containment fitting and a distal end of the coupling member.

Alternatively or additionally to any of the embodiments above, further comprising a tubular guidewire member having a proximal end and a distal end, and wherein the tubular guidewire member extends within the lumen of the inner catheter, and wherein a proximal end of the tubular guidewire member is coupled to a handle.

Alternatively or additionally to any of the embodiments above, wherein a proximal end of the actuation shaft is coupled to the handle, wherein the handle is configured to permit simultaneous translation of the actuation shaft and the tubular guidewire member.

Alternatively or additionally to any of the embodiments above, wherein the actuation shaft is fixedly attached to the tubular guidewire member.

Alternatively or additionally to any of the embodiments above, wherein the coupling member is fixedly attached to the tubular guidewire member.

Alternatively or additionally to any of the embodiments above, wherein the coupling member is fixedly attached to the tubular guidewire member.

Alternatively or additionally to any of the embodiments above, wherein the coupling member permits simultaneous rotation and translation of the actuation shaft within the lumen of the inner catheter.

Another system for implanting a heart valve includes:
a handle;
a deployment shaft having a proximal end coupled to the handle, a distal portion and a lumen extending therein;
an inner shaft extending within at least a portion of the lumen of the deployment shaft, the inner shaft having a lumen extending therein; and
a translation assembly positioned within and translatable within the lumen of the inner shaft, the translation assembly including an actuating shaft, a coupling member, a plurality of translation members and a grouping coil;
wherein the plurality of translation members each have a proximal end and a distal end, wherein the distal ends of the translation members are coupled to the implantable heart valve, and wherein the proximal ends of the translation members are coupled to a distal portion of the coupling member;
wherein the grouping coil is wound around the plurality of translation members.

Alternatively or additionally to any of the embodiments above, wherein a distal end of the actuating shaft is coupled to a proximal portion of the coupling member.

Alternatively or additionally to any of the embodiments above, wherein a length of the grouping coil is configured to adjust as the coupling member translates along the longitudinal axis of the inner shaft.

Alternatively or additionally to any of the embodiments above, wherein the grouping coil is designed to group the plurality of translation members as the translation members translate along the longitudinal axis of the inner shaft.

Alternatively or additionally to any of the embodiments above, further comprising a guidewire catheter having a proximal end and a distal end, and wherein the guidewire catheter extends within the lumen of the inner shaft, and wherein a proximal end of the guidewire catheter is coupled to the handle.

Alternatively or additionally to any of the embodiments above, wherein a proximal end of the actuating shaft is coupled to the handle, wherein the handle is configured to permit simultaneous translation of the actuating shaft and the guidewire catheter.

Alternatively or additionally to any of the embodiments above, wherein the actuating shaft is fixedly attached to the guidewire catheter.

A method for implanting an implantable heart valve at a target site includes:

advancing an implantable heart valve delivery system to a target site, the delivery system including:

an outer shaft having a proximal end, a distal portion and a lumen extending therein;

a liner having a proximal end, a distal portion and a lumen extending therein, wherein the liner extends within at least a portion of the lumen of the outer shaft;

a translation rod extending within a portion of the lumen of the liner, wherein a distal end of the translation rod is coupled to a proximal portion of a coupling member;

a plurality of translation members each having a proximal end and a distal end, wherein the distal ends of the translation members are coupled to the implantable medical device, and wherein the proximal ends of the translation members are coupled to a distal portion of the coupling member;

a plurality of support members each having a proximal end and a distal end, wherein the distal ends of the support members are coupled to the implantable heart valve, and wherein the proximal ends of the support members are coupled to a distal portion of the liner; and a grouping coil wound around the plurality of translation members;

shifting the outer shaft distally relative to the liner to partially deploy the implantable heart valve; and translating the plurality of translation members in a proximal direction relative to the support members to fully deploy the implantable heart valve at the target site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the body. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed. For example, therapies have been developed which allow a blocked coronary artery to be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

Figure 1:
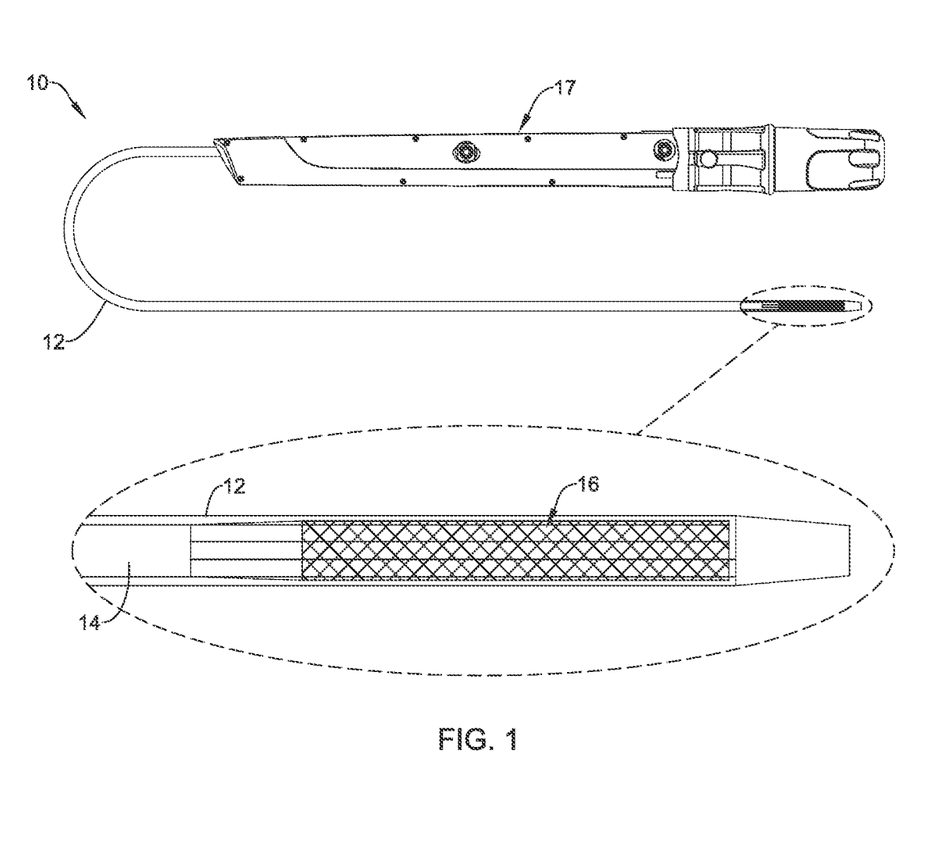
FIG. 1 is a side view of an example medical device system.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16 (shown in the detailed view of FIG. 1), such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 17 may be disposed at a proximal end of the outer sheath 12 and/or the inner catheter 14 and may include one or more actuation mechanisms associated therewith. In other words, one or more tubular members (e.g., the outer sheath 12, the inner catheter 14, etc.) may extend distally from the medical device handle 17. In general, the medical device handle 17 may be designed to manipulate the position of the outer sheath 12 relative to the inner catheter 14 and/or aid in the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1, for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 17 in order to translate the medical implant 16 into a generally shortened and larger profile "deployed" configuration suitable for implantation within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system (e.g., the medical device system 10) may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

Figure 2:
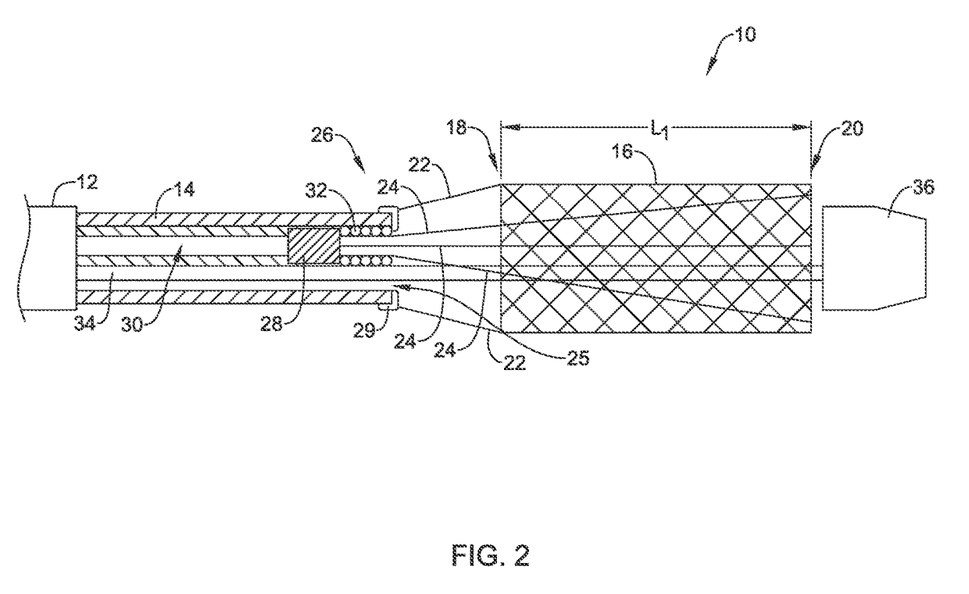
FIG. 2 is a partial cross-sectional view of a portion of an example medical device delivery system.

FIG. 2 illustrates the medical device system 10 in a partially deployed configuration. As illustrated in FIG. 2, the outer sheath 12 of the medical device system 10 has been retracted in a proximal direction to a position proximal of the medical implant 16. In other words, the outer sheath 12 has been retracted (e.g., pulled back) in a proximal direction such that it uncovers the medical device implant 16 from a compact, low-profile delivery position to a partially deployed position.

In at least some examples contemplated herein, the medical device implant 16 may be designed to self-expand once released from under the outer sheath 12. However, as shown in FIG. 2, the medical device system 10 may be designed such that the implant 16 may be restricted from expanding fully in the radial direction. For example, FIG. 2 shows medical device implant 16 having a partially deployed position denoted as a length "$L_1$."

FIG. 2 further illustrates that in some examples, the implant 16 may include one or more support members 22 coupled to the proximal end 18 of the implant 16. Further, FIG. 2 illustrates that in some examples, the implant 16 may include one or more translation members 24 coupled to the distal end 20 of the implant 16. Additionally, in some examples (such as that illustrated in FIG. 2), the translation members 24 and support members 22 may work together to maintain the implant in a partially deployed position after the outer sheath has been retracted to uncover the implant 16. For example, FIG. 2 illustrates that the support members 22 may be designed such that the distal end of each of the support members may be coupled to the proximal end of the implant 16 and that the proximal end of each of the support members 22 may be coupled to the distal end of the inner catheter 14. For example, FIG. 2 illustrates that the proximal ends of the support members 22 may be attached to a containment fitting 28 which is rigidly fixed to the distal end of the inner catheter 14. It can be further appreciated that in some instances, the support members 22 may be designed to limit the proximal movement of the proximal end 18 of the implant 16 relative to the distal end of the inner catheter 14.

Additionally, the translation members 24 may be designed to translate in a distal-to-proximal direction such that the translation of the translation members (via operator manipulation at the handle, for example) may "pull" the distal end 20 of the implant closer to the proximal end 18 of the implant 16.

Figure 3:
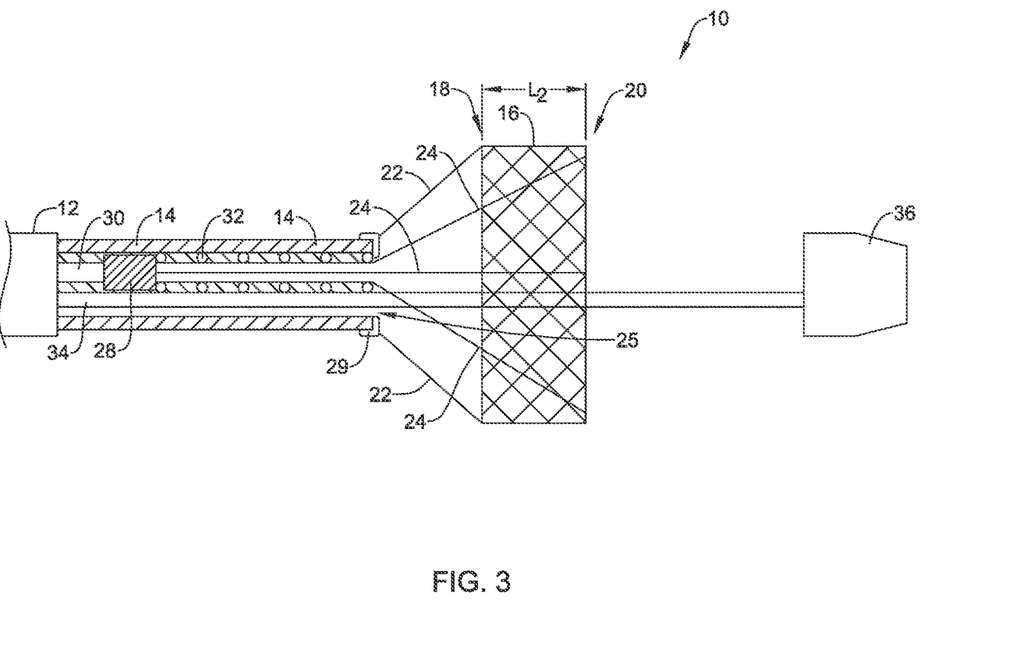
FIG. 3 is a partial cross-sectional view of a portion of an example medical device delivery system.

For example, FIG. 3 illustrates the distal-to-proximal translation of the translation members 24. It can be appreciated that if the support members 22 limit the proximal movement of the proximal end 18 of the implant 16 while the translation members 24 are translated proximally, the implant 16 may both foreshorten (along the longitudinal axis of the implant 16) and also expand radially outward. The foreshortening and radial expansion of implant 16 can be seen by comparing the shape and position of the implant 16 in FIG. 2 to the shape and position of the implant 16 in FIG. 3. The position of the implant 16 shown in FIG. 3 may be described as a fully deployed positioned of the implant 16 (versus the partially deployed positioned of the implant 16 shown in FIG. 2). Further, FIG. 3 depicts the length of the fully deployed implant 16 as $L_2$, whereby the distance $L_2$ is less than the distance $L_1$ shown in FIG. 2.

Additionally, it can be appreciated that the translation members 24 may be designed to be able extend in a proximal-to-distal direction such that they elongate (e.g., lengthen) the implant 16 (along its longitudinal axis). In other words, implant 16 may be able to shift between a partially deployed position (shown in FIG. 2) and a fully deployed position (shown in FIG. 3) through the translation (either proximal or distal) of the translation members 24 along the longitudinal axis as the support members 22 limit the movement of the proximal end 18 of the implant 16.

It should be noted that the above description and illustrations regarding the arrangement, attachment features and operation of the support members 22 and the translation members 24 as they engage and function relative to the implant 16 is schematic. It can be appreciated that the design (e.g., arrangement, attachment features, operation, etc.) of the both support member 22 and the translation members 24 as they relate and function relative to the implant 16 may vary. For example, it is possible to design, arrange and operate the translation members 24 and the support members 22 in a variety of ways to achieve the partial and full deployment configurations of the implant 16.

In some examples, an operator may be able to manipulate the translation members 24 via the handle member 17. For example, the handle 17 may include an actuation member designed to control the translation of the translation members 24. FIG. 2 illustrates that the handle member 17 may be coupled to the translation members 24 via an actuation shaft 30 and a coupling member 28. For example, as will be described in greater detail below, FIG. 2 illustrates that the proximal ends of the translation members 24 may be coupled to a distal end of the coupling member 28. Additionally, FIG. 2 further illustrates that a distal end of actuation shaft 30 may be coupled to the proximal end of the coupling member 28. Further, while not shown in FIG. 2, it can be appreciated that the actuation shaft 30 may extend within the entire length of the inner shaft 14 from the coupling member 28 to the handle member 17.

For purposes of discussion herein, the inner shaft 14 may also be referred to as an inner member or liner 14. The liner 14 may include a number of different features shown in the figures described herein. For example, the liner may include a lumen 25. Further, the translation members 24, coupler 28, actuation shaft 30, guidewire lumen 34 (described below), and grouping coil 32 (described below) may be disposed within the lumen 25. These are just examples. The inner liner 14 may vary in form. For example, the inner liner 14 may include a single lumen, multiple lumens, or lack a lumen.

As described above, FIG. 2 and FIG. 3 illustrate the translation of translation members 24 in a distal-to-proximal direction (which shortens and radially expands the implant 16, as described above). However, FIG. 3 further illustrates that translation of the translation members 24 in a distal-to-proximal direction is accomplished by translation of the actuation shaft 30 and coupling member 28 within the lumen 25 of the inner catheter 14. For example, as the actuation shaft 30 is retracted (e.g., pulled proximally within lumen 25 of the inner catheter 14), it retracts the coupling member 28 proximally, which, in turn, retracts the translation members 24 in a proximal direction.

In some instances it may be desirable to maintain translation members 24 in a substantially linear configuration as they are translated within the lumen 25 of the inner catheter 14. In some examples, therefore, medical device system 10 may include a component designed to limit and/or prevent the translation members 24 from twisting around each other within the lumen 25 of the inner catheter 14. For example, FIG. 2 and FIG. 3 illustrate a grouping coil 32 wound around the translation members 24 such that the grouping coil maintains the translation members 24 in a substantially liner configuration (and thereby limits and/or prevents the translation members 24 from twisting within lumen 25) as the translation members 24 are translated through the lumen 25 of the inner catheter 14.

FIG. 2 and FIG. 3 further illustrate that the proximal end of the grouping coil 32 may be positioned adjacent the distal end of the coupling member 28 and that the distal end of the grouping coil 32 may be positioned adjacent the distal end of the inner catheter 14. In particular, the distal end of the grouping coil 32 may be prevented from extending distally beyond the distal end of the inner catheter 14 by the containment fitting 29. In other words, the distal end of the grouping coil 32 may contact the containment fitting 29.

It can be further appreciated that the grouping coil 32 may be positioned within the lumen 25 of the inner catheter 14 such that the grouping coil 32 may elongate and shorten (e.g., a length of the grouping coil may adjust) within the lumen 25 of the inner catheter 14. For example, as the coupling member 28 is translated in a proximal direction (shown in FIG. 3 as compared to FIG. 2), the grouping coil may elongate while continuing to group and/or contain the translation members 24 in a substantially linear configuration.

FIG. 2 and FIG. 3 further illustrate that the medical device system 10 may include a tubular guidewire member 34 extending within the lumen 25 of the inner catheter 14. The tubular guidewire member 34 may be designed to permit a guidewire to extend and translate therein. Further, the tubular guidewire member 34 may extend from the handle member 17, through the lumen 25 of the inner member 14, through the implant 16 and terminate at a nosecone 36. Additionally the tubular guidewire member 34 may include a lumen (not shown in FIG. 2 or FIG. 3) that permits a guidewire to be advanced therein. In other words, the medical device 10 may be advanced to a target site within a body over a guidewire extending within the lumen of the tubular guidewire member 34.

Figure 4:
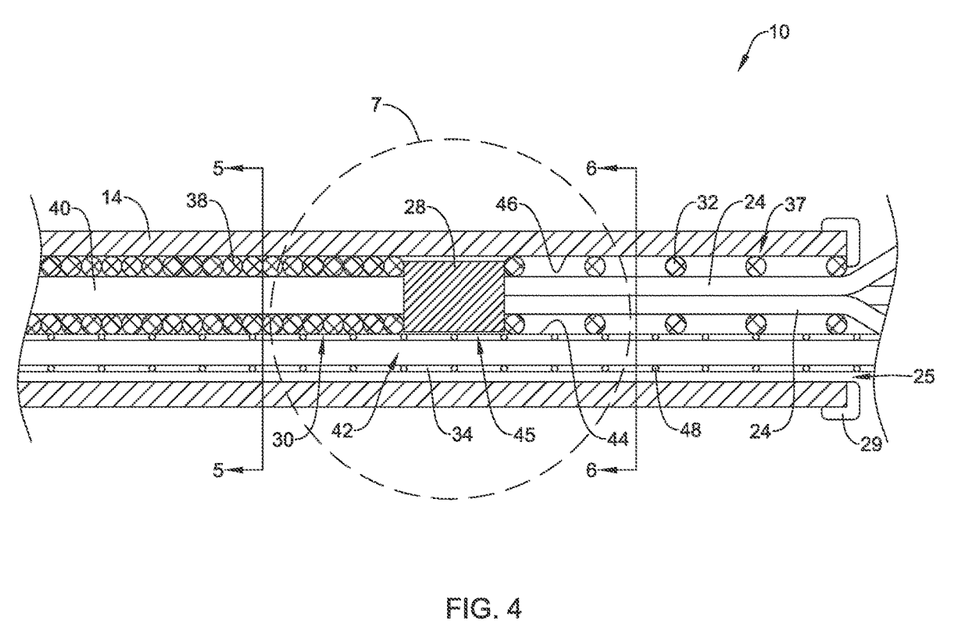
FIG. 4 is a partial cross-sectional view of a portion of the catheter shaft shown in FIGS. 1-3.

FIG. 4 illustrates a cross-section of a portion of the medical device system 10 described with respect to FIGS. 1-3. In particular, as described above, FIG. 4 illustrates the actuation shaft 30 coupled to coupler 28, translation members 24 coupled to coupler 28 and grouping coil 32 (the distal end of which is positioned adjacent the containment fitting 29, as described above) wound around the translation members 24. FIG. 4 further illustrates that the outer surface 37 of the grouping coil 32 may contact both the inner surface 46 of the inner catheter 14 and the outer surface 44 of the guidewire member 34. Therefore, it can be further appreciated that the outer diameter (and therefore the inner diameter) of the grouping coil 32 may remain constant as the grouping coil lengthens or shortens as the coupler 28 translates within the lumen 25 of the inner catheter 14.

Additionally, it can be appreciated that the medical device system 10 may be designed such that both the proximal end and the distal end of the grouping coil 32 may not be fixedly attached to adjacent structures (e.g., may not be attached to the coupling member 28 and/or the containment fitting 29). It can be appreciated that by not attaching either end of the grouping coil 32 to an adjacent structures (e.g., the coupling member 28 and/or the containment fitting 29), the grouping coil 32 is permitted to twist freely while lengthening or shortening within the lumen 25. This freedom of movement allows the grouping coil 32 to maintain an inner diameter which tightly groups (e.g., contains) the translation members 24 to each other as that translate linearly within the lumen 25 of inner catheter 14.

FIG. 4 further illustrates that coupler 28 may be positioned within the lumen 25 of the inner catheter 14 such that the bottom surface 45 of the coupler 28 is adjacent to the outer surface 44 of the guidewire member 34. In some examples, the coupler 28 may be designed such that it is not rigidly fixed to the guidewire member 34, and therefore, may translate relative to the guidewire member 34. In other examples, the coupler 28 may be designed such that it is rigidly fixed to the guidewire member 34, and therefore, translation of coupler 28 (which itself may occur via translation of the actuation shaft 30) may also translate both the guidewire member 34 and the translation members 24. In other words, it can be appreciated that in instances where the coupler 28 is rigidly fixed to the guidewire member 34, an operator manipulating the actuation shaft 30 via handle 17 may translate both the translation members 24 and the guidewire member 34 together such that distal or proximal translation of either the translation members 24 or the guidewire member 34 will translate both the translation members 24 or the guidewire member 34 a correspondingly equal amount. Further, it can be appreciated the same effect may be achieved by coupling the guidewire member 34 and the actuation shaft 30 anywhere along medical device system 10, including coupling the guidewire member 34 and the actuation shaft 30 to one another in the handle member 17. It can be appreciated that the guidewire member 34 and the actuation shaft 30 may be coupled together in more than one location along medical device system 10.

In some instances, it may be desirable for the nosecone 36 to translate in a proximal direction as the implantable medical device 16 shifts from a collapsed configuration to a fully deployed configuration (as shown in FIGS. 1-3). It can be appreciated from the above discussion that because the nosecone 36 is connected to the distal end of the guidewire member 34, that as the guidewire member 34 translates with the translation members 24 (via the coupler 28 and actuation shaft 30), the nosecone 36 with correspondingly translate in a proximal direction as the translational members act to shift the implantable medical device 16 from a collapsed to a fully deployed configuration.

FIG. 4 further illustrates that in some instances actuation shaft 30 may include an actuation rod 40 positioned within the lumen of a coil member 38. Similar to that described above with respect to the grouping coil 32, the outer surface of the coil member 38 may contact both the inner surface 46 of the inner catheter 14 and the outer surface 44 of the guidewire member 34. It can be appreciated that the outer surface of the coil member 38 may reduce the frictional forces of actuation shaft 30 along the inner surface 46 of the inner catheter 14 as compared to the frictional forces that would be present if the actuation shaft 30 did not include a coil member. For example, coil member 38 provides both "point to point" contacts along the inner surface 46 of the inner member 14 in addition to increasing the ease with which the actuation shaft flexes/bends within the lumen 25 of inner catheter 14. These properties reduce the overall surface friction between the outer surface of actuation shaft 30 and the inner surface 46 of inner catheter 14 (as compared to a solid rod of similar proportions). The reduction in friction may further reduce the likelihood of the actuation shaft 30 to store and release energy in the form of a "backlash" effect. It is contemplated that the coil member 38 may be extend along a portion of or the entire length of the actuation rod 40. Further, the actuation rod 40 may extend from the proximal end of the coupler 28 to the handle member 17. Additionally, the above described functional characteristics of the coil member 38 are not intended to be limiting. For example, it is contemplated that the coil member 38 may be utilized to conduct electricity along a portion thereof (e.g., along the surface or other portion of coil member 38).

FIG. 4 further illustrates that in some examples guidewire member 34 may include a reinforcing coil embedded with its tubular wall. For example, FIG. 4 shows coil 48 positioned with the wall of guidewire member 34. Coil 48 may provide additional strength and flexibility to the guidewire member 34. Additionally, FIG. 4 illustrates the lumen 42 of the guidewire member 34. It can be appreciated that a guidewire (not shown) may extend with the lumen 42 of the guidewire member 34.

Figure 5:
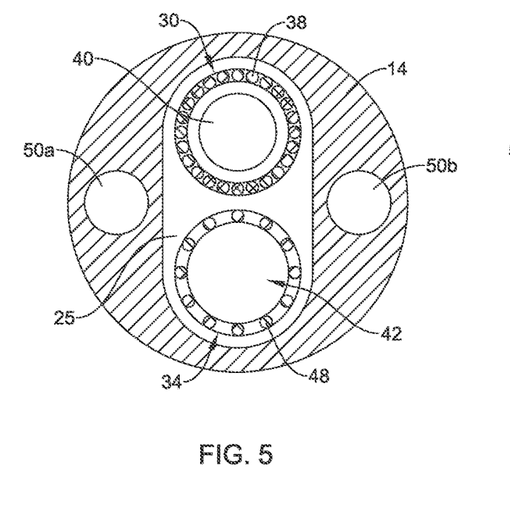
FIG. 5 is a cross-sectional view along line 5-5 of FIG. 4.

FIG. 5 illustrates a cross-sectional view along line 5-5 of FIG. 4. As indicated above, the inner catheter 14 may include a number of features. For example, the inner catheter 14 may include one or more tension resistance members 50a/50b. The tension resistance members 50a/50b may take the form of a wire (e.g., a metallic wire), a braid, cable, stranded cable, a composite structure, or the like. In one example, the tension resistance members 50a/50b are both metallic wires. In another instance, the tension resistance members 50a/50b are both metallic braids. The braids may further includes an axial wire made from a suitable polymer or metal (e.g., aramid). The tension resistance members 50a/50b may be made from the same materials and/or have the same configuration. Alternatively, the tension resistance members 50a/50b may be different from one another. Furthermore, while FIG. 2 illustrates that the inner catheter 14 includes two tension resistance members 50a/50b, this is not intended to be limiting. Other numbers of tension resistance members 50a/50b are contemplated such as one, three, four, five, six, seven, or more.

FIG. 5 further illustrates that the shape of the lumen 25 of the inner catheter 14 may be designed to limit twisting of the actuation shaft 30 and the guidewire member 34. For example, FIG. 5 illustrates that lumen 25 may be non-circular. For example, the shape of the lumen 25 may be ovular, square, rectangular, etc. It can be appreciated that as the inner catheter 14 rotates within the lumen of the outer member 12, the shape of the lumen 25 may force both the actuation shaft 30 and the guidewire member 34 to maintain the respective spatial relationship as depicted in FIG. 5. In other words, the shape of the lumen 25 forces the actuation shaft 30 and the guidewire member 34 to remain in their positions relative to one another independent of the bending, rotating, flexing, etc. of the inner catheter 14.

Additionally, FIG. 5 also illustrates the actuation shaft 30 and the guidewire member positioned adjacent one another within lumen 25. As described above, actuation shaft 30 may include an actuation rod 40 positioned within the lumen of a coil member 38. Additionally, FIG. 5 shows guidewire member 34. The guidewire member 34 may include a reinforcing coil 48 embedded with its tubular wall. For example, FIG. 5 shows coil 48 positioned with the wall of guidewire member 34. Coil 48 may provide additional strength and flexibility to the guidewire member 34. Additionally, FIG. 5 illustrates the lumen 42 of the guidewire member 34.

Figure 6:
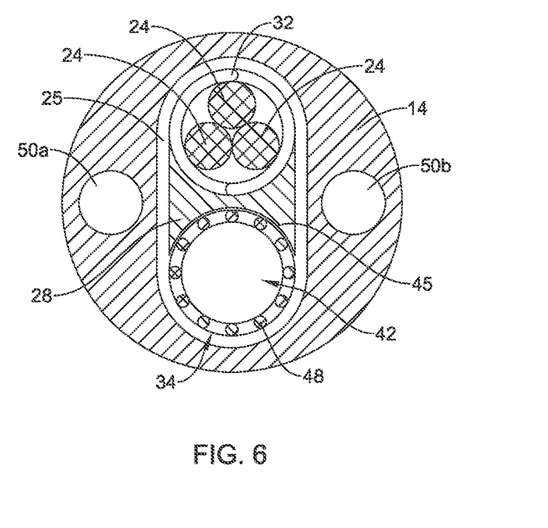
FIG. 6 is a cross-sectional view along line 6-6 of FIG. 4.

FIG. 6 illustrates a cross-sectional view along line 6-6 of FIG. 4. FIG. 4 shows grouping coil 32, coupler 28 and guidewire member 34 positioned within lumen 25. Additionally, FIG. 6 shows that the grouping coil 32 may surround three translational members 24 positioned therein. The translational members 24 may be spaced equidistance from one another. For example, the translational members 24 may be spaced at substantially 120 degree angles relative to one another. Further, while FIG. 6 shows three translational members 24, it is contemplated that more or less than three translational members 24 may be utilized within medical device system 10. For example, medical device system 10 may include 1, 2, 3, 4, 5, 6, 7, 8, 9, 10 or more translational members 24.

Additionally, FIG. 6 illustrates that inner catheter 14 may include one or more tension resistance members 50a/50b. The tension resistance members 50a/50b may take the form of a wire (e.g., a metallic wire), a braid, cable, stranded cable, a composite structure, or the like. Further, FIG. 6 illustrates that tension resistance members 50a/50b may be positioned opposite one another on either side of lumen 25.

Additionally, FIG. 5 shows guidewire member 34. The guidewire member 34 may include a reinforcing coil 48 embedded with its tubular wall. For example, FIG. 5 shows coil 48 positioned with the wall of guidewire member 34. Coil 48 may provide additional strength and flexibility to the guidewire member 34. Additionally, FIG. 5 illustrates the lumen 42 of the guidewire member 34.

FIG. 6 further illustrates the coupler 28 including the bottom surface 45 (described above). As illustrated, the bottom surface 45 is shaped to mate with the outer surface the guidewire member 34. For example, in some examples, the bottom surface 45 may include a curved portion which mates with the radius defined by the outer surface 44 of the guidewire member 34. As described above, the bottom surface 45 of the coupler 28 may or may not be rigidly fixed to the guidewire member 34.

Figure 7:
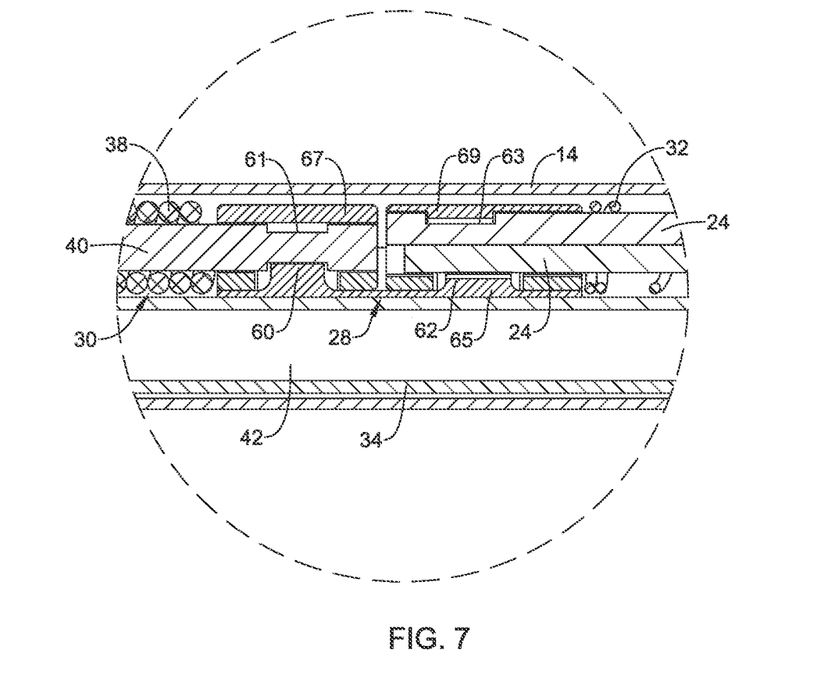
FIG. 7 is a partial cross-sectional view of a portion of an example medical device delivery system.

FIG. 7 illustrates a detailed view of a portion of the medical device system 10 shown in FIG. 6. Further, FIG. 7 illustrates a cross-sectional view of coupler 28. Coupler 28 may include a base member 65, a first cap 67 and a second cap 69. First cap 67 and second cap 69 may be separate components from base member 65. Further, first cap 67 and second cap 69 may be attached to base member 65 via welding or any other suitable process.

As shown, a portion of the actuation rod 40 may extend into a portion of coupler 28 and thereby contact both base member 65 and first cap 67. Similarly, portions of the translational members 24 may extend into a portion of coupler 28 and thereby contact both base member 65 and first cap 69. It can be appreciated from FIG. 7 that base member 65 may include one or more projections 60 that mate with one or more recess 61 in the actuation rod 40. Similarly, it can be appreciated from FIG. 7 that base member 65 may include one or more projections 62 that mate with one or more recesses 63 in the translational members 24. It can further be appreciated that engaging a respective projection with a recess portion (in both the actuation rod 40 and the translational members 24) may limit translational movement of both the actuation rod 40 and the translational members 24 relative to the coupler. In other words, engagement of a respective projection with a recess portion (in both the actuation rod 40 and the translational members 24) may prevent both the actuation rod 40 and the translational members 24 from translating independently of the coupler 28 (and one another). However, it can be further appreciated that the engagement of a respective projection with a recess portion (in both the actuation rod 40 and the translational members 24) may permit the actuation rod 40 to spin/swivel on its own longitudinal axis. Additionally, it can be appreciated that coupler 28 (including base member 65, first cap 67 and second cap 69) may permit dissimilar materials to be engaged because they are mechanically "trapped" and preferentially oriented within coupler 28. In some instances, the coupler 28 may be defined as a "swivel."

The materials that can be used for the various components of the medical devices and/or system 10 disclosed herein may include those commonly associated with medical devices. However, this is not intended to limit the devices and methods described herein, as the discussion may be applied to other components of the medical devices and/or systems 10 disclosed herein including the various shafts, liners, components described relative thereto.

The medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MRI) compatibility is imparted into the medical device 10. For example, the medical device 10 may include a material that does not substantially distort the image and create substantial artifacts (e.g., gaps in the image). Certain ferromagnetic materials, for example, may not be suitable because they may create artifacts in an MRI image. The medical device 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A system for delivering an implantable medical device, comprising:
    an outer shaft having a proximal end, a distal portion and a lumen extending therein;
    an inner catheter having a proximal end, a distal portion and a lumen extending therein, wherein the inner catheter extends within at least a portion of the lumen of the outer shaft;
    an actuation shaft extending within a portion of the lumen of the inner catheter, wherein a distal end of the actuation shaft is coupled to a proximal portion of a coupling member;
    a plurality of translation members each having a proximal end and a distal end, wherein the distal ends of the translation members are coupled to the implantable medical device, and wherein the proximal ends of the translation members are coupled to a distal portion of the coupling member; and
    a grouping coil wound around at least a portion of each of the plurality of translation members.

2. The system of claim 1, wherein the actuation shaft, the plurality of translation members and the coupling member are configured to translate along the longitudinal axis of the inner catheter.

3. The system of claim 2, wherein a length of the grouping coil is configured to adjust as the coupling member translates along the longitudinal axis of the inner catheter.

4. The system of claim 3, wherein the grouping coil is designed to group the plurality of translation members as the translation members translate along the longitudinal axis of the inner catheter.

5. The system of claim 1, further comprising a containment fitting attached to the distal portion of the inner catheter, wherein the containment fitting is configured to limit a distal end of the grouping coil from translating distally.

6. The system of claim 5, wherein the grouping coil is positioned between the containment fitting and a distal end of the coupling member.

7. The system of claim 1, further comprising a tubular guidewire member having a proximal end and a distal end, and wherein the tubular guidewire member extends within the lumen of the inner catheter, and wherein a proximal end of the tubular guidewire member is coupled to a handle.

8. The system of claim 7, wherein a proximal end of the actuation shaft is coupled to the handle, wherein the handle is configured to permit simultaneous translation of the actuation shaft and the tubular guidewire member.

9. The system of claim 8, wherein the actuation shaft is fixedly attached to the tubular guidewire member.

10. The system of claim 8, wherein the coupling member is fixedly attached to the tubular guidewire member.

11. The system of claim 9, wherein the coupling member is fixedly attached to the tubular guidewire member.

12. The system of claim 1, wherein the coupling member permits simultaneous rotation and translation of the actuation shaft within the lumen of the inner catheter.

13. A system for implanting a heart valve, comprising:
    a handle;
    a deployment shaft having a proximal end coupled to the handle, a distal portion and a lumen extending therein;
    an inner shaft extending within at least a portion of the lumen of the deployment shaft, the inner shaft having a lumen extending therein; and
    a translation assembly positioned within and translatable within the lumen of the inner shaft, the translation assembly including an actuating shaft, a coupling member, a plurality of translation members and a grouping coil;
    wherein the plurality of translation members each have a proximal end and a distal end, wherein the distal ends of the translation members are coupled to the implantable heart valve, and wherein the proximal ends of the translation members are coupled to a distal portion of the coupling member;
wherein the grouping coil is wound around the plurality of translation members.

14. The system of claim 13, wherein a distal end of the actuating shaft is coupled to a proximal portion of the coupling member.

15. The system of claim 13, wherein a length of the grouping coil is configured to adjust as the coupling member translates along the longitudinal axis of the inner shaft.

16. The system of claim 13, wherein the grouping coil is designed to group the plurality of translation members as the translation members translate along the longitudinal axis of the inner shaft.

17. The system of claim 13, further comprising a guidewire catheter having a proximal end and a distal end, and wherein the guidewire catheter extends within the lumen of the inner shaft, and wherein a proximal end of the guidewire catheter is coupled to the handle.

18. The system of claim 17, wherein a proximal end of the actuating shaft is coupled to the handle, wherein the handle is configured to permit simultaneous translation of the actuating shaft and the guidewire catheter.

19. The system of claim 18, wherein the actuating shaft is fixedly attached to the guidewire catheter.

\* \* \* \* \*